(12) United States Patent
Winarta et al.

(10) Patent No.: US 6,258,229 B1
(45) Date of Patent: Jul. 10, 2001

(54) DISPOSABLE SUB-MICROLITER VOLUME SENSOR AND METHOD OF MAKING

(76) Inventors: Handani Winarta, 18 Hyacinth Dr., Nashua, NH (US) 03062; Xiaohua Cai, 19 McCulloch St., Needham, MA (US) 02494; Fung Seto, 31 Pratt Dr., Newton, MA (US) 02465; Chung Chang Young, 145 Buckskin Dr., Weston, MA (US) 02193

( * ) Notice: Subject to any disclaimer, the term of this patent is extended or adjusted under 35 U.S.C. 154(b) by 0 days.

(21) Appl. No.: 09/324,493

(22) Filed: Jun. 2, 1999

(51) Int. Cl.[7] .............................. G01N 27/26; A61B 5/08; H02B 13/00
(52) U.S. Cl. ..................... 204/403; 204/412; 427/2.13; 216/13
(58) Field of Search .................................. 204/400, 403, 204/412, 416, 431, 280, 286; 422/82.01, 88.02, 82.03; 324/439; 427/2.13; 216/13

(56) References Cited

U.S. PATENT DOCUMENTS

| | | |
|---|---|---|
| 4,897,173 | 1/1990 | Nankai et al. . |
| 5,120,420 | 6/1992 | Nankai et al. . |
| 5,232,856 * | 8/1993 | Firth ................................ 435/285.2 |
| 5,264,103 | 11/1993 | Yoshioka et al. . |
| 5,266,179 | 11/1993 | Nankai et al. . |
| 5,288,636 | 2/1994 | Pollman et al. . |
| 5,382,346 | 1/1995 | Uenoyama et al. . |
| 5,395,504 | 3/1995 | Saurer et al. . |
| 5,437,999 * | 8/1995 | Diebold et al. ................... 435/287.9 |
| 5,496,453 | 3/1996 | Uenoyama et al. . |
| 5,508,171 | 4/1996 | Walling et al. . |
| 5,509,410 | 4/1996 | Hill et al. . |
| 5,563,067 * | 10/1996 | Sugihara et al. .................. 435/287.1 |
| 5,628,890 | 5/1997 | Carter et al. . |
| 5,670,031 * | 9/1997 | Hintsche et al. ..................... 204/412 |
| 5,682,884 | 11/1997 | Hill et al. . |
| 5,708,247 | 1/1998 | McAleer et al. . |
| 5,755,953 | 5/1998 | Henning et al. . |
| 5,759,364 | 6/1998 | Charlton et al. . |
| 5,762,770 | 6/1998 | Pritchard et al. . |
| 6,004,441 * | 12/1999 | Fujiwara et al. ..................... 204/412 |

OTHER PUBLICATIONS

CAPLUS abstract of Jezkova et al. ("stabilization of an osmium bis–bipyridyl polymer–modified carbon paste amperometric glucose biosensor using polyethyleneimine", Electroanalysis (1997), 9(13), 978–984), Month Unknown.*
WO 98/35225 PCT Application, Aug. 13, 1998, Adam Heller et al.
WO 98/55856 PCT Application, Dec. 10, 1998, Stephen Williams et al.

* cited by examiner

Primary Examiner—T. Tung
Assistant Examiner—Alex Noguerola
(74) Attorney, Agent, or Firm—Robert R. Deleault, Esq.; Mesmer & Deleault, PLLC

(57) ABSTRACT

A disposable electrode strip for testing a fluid sample including a laminated strip with a first and second end, a vent, an open path for receiving a fluid sample of less than one microliter beginning from the first end and connecting to the vent, a working electrode, a reference electrode and a pseudo-working electrode embedded in the laminated strip within the open path and proximate to the first end, a reagent matrix coextensive within the open path and covering the three electrodes, and conductive contacts located at the second end of the laminated strip.

38 Claims, 6 Drawing Sheets

DISPOSABLE SUB-MICROLITER VOLUME SENSOR AND METHOD OF MAKING

BACKGROUND OF THE INVENTION

1. Field of the Invention

The present invention relates generally to electrochemical sensors that can be used for the quantification of a specific component or analyte in a liquid sample. Particularly, this invention relates to a new and improved electrochemical sensor and to a new and improved method of fabricating electrochemical sensors. More particularly, this invention relates to a disposable electrochemical sensor that is inexpensive to manufacture. Even more particularly, this invention relates to a disposable electrochemical sensor that gives accurate readings and requires only about 0.2 microliter of fluid sample. Still even more particularly, this invention relates to disposable electrochemical sensors which are used for performing electrochemical assays for the accurate determination of analytes in physiological fluids.

2. Description of the Prior Art

Biosensors have been used in the determination of concentrations of various analytes in fluids for more than three decades. Of particular interest is the measurement of blood glucose. It is well known that the concentration of blood glucose is extremely important for maintaining homeostasis. Products that measure fluctuations in a person's blood sugar, or glucose levels, have become everyday necessities for many of the nation's millions of diabetics. Because this disorder can cause dangerous anomalies in blood chemistry and is believed to be a contributor to vision loss and kidney failure, most diabetics need to test themselves periodically and adjust their glucose level accordingly, usually with insulin injections. If the concentration of blood glucose is below the normal range, patients can suffer from unconsciousness and lowered blood pressure which may even result in death. If the blood glucose concentration is higher than the normal range, the excess blood glucose can result in synthesis of fatty acids and cholesterol, and in diabetics, coma. Thus, the measurement of blood glucose levels has become a daily necessity for diabetic individuals who control their level of blood glucose by insulin therapy.

Patients who are insulin dependent are instructed by doctors to check their blood-sugar levels as often as four times a day. To accommodate a normal life style to the need of frequent monitoring of glucose levels, home blood glucose testing was made available with the development of reagent strips for whole blood testing.

One type of blood glucose biosensors is an enzyme electrode combined with a mediator compound which shuttles electrons between the enzyme and the electrode resulting in a measurable current signal when glucose is present. The most commonly used mediators are potassium ferricyanide, ferrocene and its derivatives, as well as other metal-complexes. Many sensors based on this second type of electrode have been disclosed. Examples of this type of device are disclosed in the following patents.

U.S. Pat. No. 5,628,890 (1997, Carter et al.) discloses an electrode strip having an electrode support, a reference or counter electrode disposed on the support, a working electrode spaced from the reference or counter electrode on the support, a covering layer defining an enclosed space over the reference and working electrodes and having an aperture for receiving a sample into the enclosed space, and a plurality of mesh layers interposed in the enclosed space between the covering layer and the support. The covering layer has a sample application aperture spaced from the electrodes. The working electrode includes an enzyme capable of catalyzing a reaction involving a substrate for the enzyme and a mediator capable of transferring electrons between the enzyme-catalyzed reaction and the working electrode.

This device proposes to reduce the effect of hematocrit on the sensor readings. According to the disclosure, this results from the downstream spacing of the reference electrode relative to the working electrode in combination with the thin layer of the sample solution created by the mesh layers.

U.S. Pat. No. 5,708,247 (1998, McAleer et al.) discloses a disposable glucose test strip having a substrate, a reference electrode, a working electrode, and a means for making an electrical connection. The working electrode has a conductive base layer and a coating layer disposed over the conductive base layer. The coating layer is a filler having both hydrophobic and hydrophilic surface regions which form a network, an enzyme and a mediator.

U.S. Pat. No. 5,682,884 (1997, Hill et al.) discloses a strip electrode with screen printing. The strip has an elongated support which includes a first and second conductor each extending along the support. An active electrode, positioned to contact the liquid mixture and the first conductor, has a deposit of an enzyme capable of catalyzing a reaction and an electron mediator. A reference electrode is positioned to contact the mixture and the second conductor.

U.S. Pat. No. 5,759,364 (1998, Charlton et al.) discloses an electrochemical biosensor having an insulating base plate bearing an electrode on its surface which reacts with an analyte to produce mobile electrons. The base plate is mated with a lid of deformable material which has a concave area surrounded by a flat surface so that when mated to the base plate there is formed a capillary space into which a fluid test sample can be drawn. The side of the lid facing the base is coated with a polymeric material which serves to bond the lid to the base plate and to increase the hydrophilic nature of the capillary space.

U.S. Pat. No. 5,762,770 (1998, Pritchard et al.) discloses an electrochemical biosensor test strip that has a minimum volume blood sample requirement of about 9 microliters. The test strip has a working and counter electrodes that are substantially the same size and made of the same electrically conducting material placed on a first insulating substrate. Overlaying the electrodes is a second insulating substrate which includes a cutout portion that forms a reagent well. The cutout portion exposes a smaller area of the counter electrode than the working electrode. A reagent for analysis of an analyte substantially covers the exposed areas of the working and counter electrodes in the reagent well. Overlaying the reagent well and affixed to the second insulating substrate is a spreading mesh that is impregnated with a surfactant.

U.S. Pat. No. 5,755,953 (1998, Henning et al.) discloses a reduced-interference biosensor. The device generally comprises an electrode used to electrochemically measure the concentration of an analyte of interest in a solution. The device includes a peroxidase enzyme covalently bound to microparticle carbon and retained in a matrix in intimate contact with the electrode. According to this disclosure, it is the enzyme/microparticle carbon of the device which provides a composition which is displays little sensitivity to known interfering substances.

U.S. Pat. No. 5,120,420 (1992, Nankai et al.) discloses a biosensor with a base board having an electrode system mainly made of carbon, an insulating layer, a reaction layer containing an enzyme layer thereon, a spacer and a cover. The spacer creates a channel with an inlet and an outlet for holding a sample.

PCT Patent Application No. WO 98/35225 (1998, Heller et al.) discloses a sensor designed to determine the amount and concentration of an analyte in a sample having a volume of less than about one microliter. The sensor has facing working and reference electrodes with an optional sorbent spacer. The working electrode is coated with a reagent layer containing a non-leachable redox mediator and an enzyme. This device, which is capable of using a test sample volume of less than 1 microliter, requires the use of a sorbent material within the sample chamber in order to reduce the volume requirement and to introduce a hydrophilic character to the chamber in order for the sample to flow into such chamber.

However, most of the remaining prior art devices require a test sample volume of greater than 2 microliters. This volume of test sample can only be obtained from a patient, for example, using a needle and syringe, or by lancing a portion of the skin such as the fingertip and "milking" the area to obtain a useful sample volume. These procedures are inconvenient for the patient, and often painful, particularly when frequent samples are required. Less painful methods for obtaining a sample are known such as lancing the arm or thigh, which have a lower nerve ending density. However, lancing the body in the arm or thigh typically produces submicroliter sample volumes of blood because these areas are not heavily supplied with near-surface capillary blood vessels. Because the present invention requires as little as 0.2 microliters of blood, patients who must make several blood glucose measurements a day may obtain blood samples from these preferred areas.

Additional shortcomings of the prior art devices are that they have a more limited linear range, usually up to about 600 mg/dL. Further, they require a relatively longer waiting time for development of a steady-state response before a reading can be achieved.

Because of the importance of obtaining accurate glucose readings, it would be highly desirable to develop a reliable and user-friendly electrochemical sensor which does not have all of the drawbacks mentioned above. Therefore what is needed is an electrochemical sensor which requires less sample volume than previously required by the prior art. What is further needed is an electrochemical sensor which has a wide linear measurement range; that is, a sensor useable over a wider glucose concentration. What is still further needed is an electrochemical sensor which has a relatively short wait time for development of a steady-state response.

SUMMARY OF THE INVENTION

It is an object of the present invention to provide an improved electrochemical sensor which combines an enzyme and a mediator. It is a further object of the present invention to provide an electrochemical sensor which requires less sample volume than previously required by the prior art. It is still another object of the present invention to provide an electrochemical sensor which can measure a small volume of sample without the use of a mesh layer in the sample path. It is yet another object of the present invention to provide an electrochemical sensor which has a wide linear measurement range and a relatively short wait time for development of a steady-state response.

The present invention achieves these and other objectives by providing an electrochemical sensor which requires a sample size of only about 0.2 microliters and does not use a mesh layer in the sample path as a means of achieving a reduced size of the sample. Further the present invention uses a reagent composition which allows readings, which correlate very closely to the analyte concentration in the fluid sample, to be taken 20 seconds after the fluid sample enters the sample channel. The present invention has a laminated, elongated body having a sample fluid channel connected between an opening on one end of the laminated body and a vent hole spaced from the opening. The sample fluid channel is sized to optimize the quick flow of a sample such as whole blood into the channel. The rapid uptake of the sample allows the electrode reactions to reach steady-state faster, thus resulting in obtaining an analyte reading more quickly. Within the fluid channel lies at least one working electrode and a reference electrode, preferably a working electrode, a reference electrode and a pseudo-working electrode. The arrangement of the working electrode and the reference electrode is not important for purposes of the results obtained from the electrochemical sensor. The working electrode, the reference electrode and the pseudo-working electrode are each in electrical contact with separate conductive conduits, respectively. The separate conductive conduits terminate and are exposed for making an electrical connection to a reading device on the end opposite the open channel end of the laminated body.

The laminated body has a base insulating layer made from a plastic material. The base insulating layer has a conductive layer on one side. The conductive layer may be deposited on the insulating layer by screen printing, by vapor deposition, or by any method that provides for a conductive layer which adheres to the base insulating layer and substantially covers all of the base insulating layer. The vapor-deposited conductive layer is separated into conductive conduits by etching/scribing the conductive layer. The etching process may be accomplished chemically, by mechanically scribing lines in the conductive layer, by using a laser to scribe the conductive layer into separate conductive conduits, or by any means that will cause a break between and among the separate conductive conduits required by the present invention. The preferred conductive coatings are gold film or a tin oxide/gold film composition/layer.

It should be pointed out that the gold film or tin oxide/gold film itself cannot function as a reference electrode. To make the reference electrode work, there must be a redox reaction (e.g., $Fe(CN)_6^{3-}+e^-\rightarrow Fe(CN)_6^{4-}$) at the electrically conducting material when a potential is applied. Therefore, a redox mediator must be present at the conducting material used for the reference electrode.

The unique feature of the present invention is its ability to measure sample sizes as small as 0.15 microliters without using opposing working and reference electrodes and a sorbent/mesh layer therebetween to reduce the required sample volume for measurement. This is possible because of the combination of material used for the base insulating layer with conductive coating, and the unique method of forming the conductive conduits thereon.

The laminated body also has a middle insulating layer on top of the base layer. The middle layer is also made of a plastic insulating material and creates the sample fluid channel of the laminated body. It contains a U-shaped cutout on one end which overlays the electrode portion of the conductive conduits on the base layer with the open end corresponding to the open end of the laminated body described earlier.

The thickness of the middle layer must be of sufficient thickness for loading a sufficient amount of chemical reagent for use as an electrochemical sensor while maintaining a flow-channel dimension having optimum blood flow characteristics. The U-shaped cutout contains chemical reagent. The chemical reagent has a redox mediator with at least one of a stabilizer, a binder, a surfactant, a buffer, and an enzyme capable of catalyzing a reaction involving a substrate for the enzyme. The redox mediator is capable of transferring electrons between the enzyme-catalyzed reaction and the working electrode. It also makes the reference electrode function.

The laminated body of the present invention has a top layer with a vent opening. The vent opening is located such that at least a portion of the vent opening overlays the bottom of the U-shaped cutout exposing a portion of the chemical reagent of the middle insulating layer. The vent allows air within the sample fluid channel to escape as the sample fluid enters the open end of the laminated body. The sample fluid generally fills the sample fluid channel by capillary action. In small volume situations, the extent of capillary action is dependent on the hydrophobic/hydrophilic nature of the surfaces in contact with the fluid undergoing capillary action. This is also known as the wetability of the material. Capillary forces are enhanced by either using a hydrophilic insulating material to form the top layer, or by coating at least a portion of one side of a hydrophobic insulating material with a hydrophilic substance in the area of the top layer that faces the sample fluid channel between the open end of the laminated body and the vent opening of the top layer. It should be understood that an entire side of the top layer may be coated with the hydrophilic substance and then bonded to the second middle layer.

The three layers of the laminated body may be made from any dielectric material. The preferred material is a plastic material. Examples of acceptable compositions for use as the dielectric material are polyvinyl chloride, polycarbonate, polysulfone, nylon, polyurethane, cellulose nitrate, cellulose propionate, cellulose acetate, cellulose acetate butyrate, polyester, acrylic, and polystyrene.

The electrode portions, located within the sample fluid channel, contain reagent material for the working electrode (W), the reference electrode (R) and the pseudo-working electrode ($W_O$). A reagent mix is disposed into the fluid channel thus covering the electrode portions of the base insulating layer and the conductive conduits. A sufficient amount of reagent mix is deposited within the U-shaped cutout of the middle insulating layer to substantially cover all of the conductive surface delineated by the U-shaped cutout. The amount of the reagent mix used is such that the reagent matrix created upon drying is sufficient for use as an electrochemical sensor yet provides enough empty space above the reagent matrix to allow rapid blood flow through the fluid channel. The reagent matrix has a redox mediator with at least one of a stabilizer, a binder, a surfactant, a buffer, and an enzyme capable of catalyzing a reaction involving a substrate for the enzyme.

The possible electrode arrangements within the sample fluid channel may be $W$-$R$-$W_O$, $W$-$W_O$-$R$, $R$-$W$-$W_O$, $R$-$W_O$-$W$, $W_O$-$W$-$R$ or $W_O$-$R$-$W$ with the arrangement listed as the arrangement of electrodes would appear from the open end of the laminated body to the vent opening. The preferred position was found to be $R$-$W$-$W_O$; that is, as the sample fluid entered the open end of the laminated body, the fluid would cover R first, then W, then $W_O$.

The pseudo-working electrode, $W_O$, is positioned so that the sample fluid reaches it last. The resulting current at $W_O$ thus triggers the reading meter to start the measurement and analyte concentration determination process. Such an arrangement obviates reliability and accuracy problems due to an insufficient sample fluid size. It should be pointed out that $W_O$ can also be used as a counter electrode. The resulting three-electrode system (i.e. working electrode, reference electrode and counter electrode) would be used in the case of a sample fluid having a large IR drop. It should also be pointed out that $W_O$, combined with R, can be used to measure the resistance of the sample fluid. The resulting resistance could be used to estimate the hematocrit of a blood sample and therefore to correct the hematocrit interference.

All of the advantages of the present invention will be made clearer upon review of the detailed description, drawings and appended claims.

DETAILED DESCRIPTION OF THE PREFERRED EMBODIMENT

Figure 1:
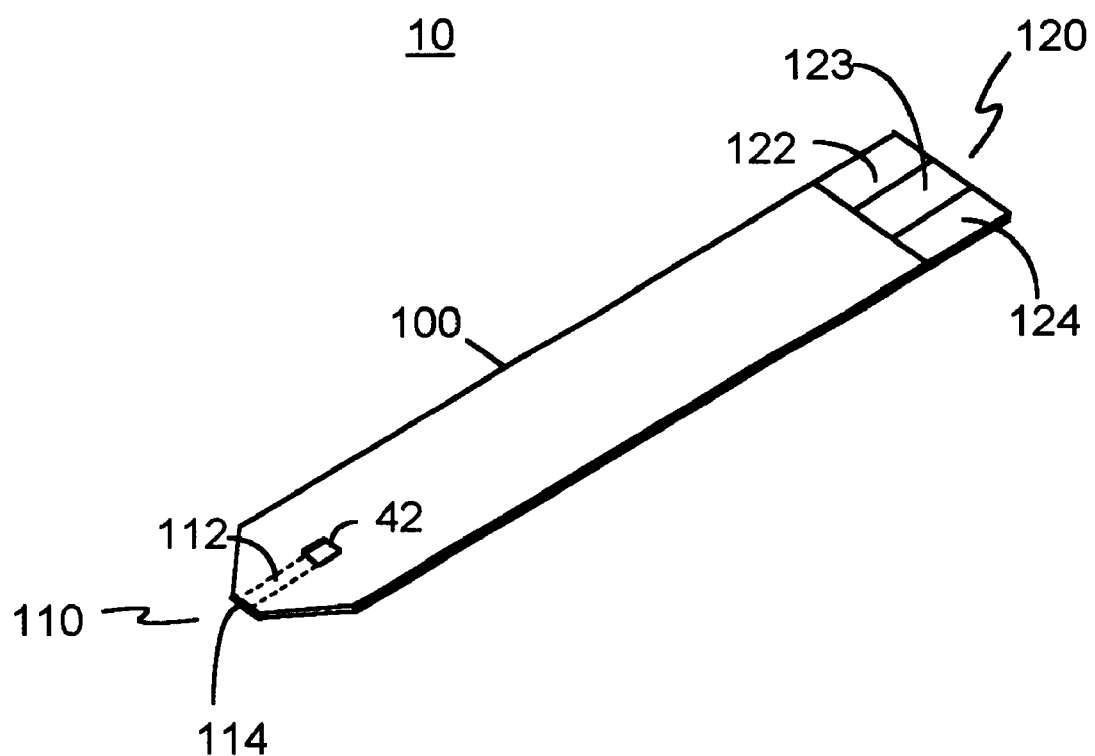
FIG. 1 is a perspective view of the present invention showing the open end, the vent and the electrical contact points of the laminated body.

The preferred embodiment of the present invention is illustrated in FIGS. 1–6. FIG. 1 shows a sensor 10 of the present invention. Sensor 10 has a laminated body 100, a fluid sampling end 110, an electrical contact end 120, and a vent opening 42. Fluid sampling end 110 includes a sample fluid channel 112 between a sampling end aperture 114 and vent opening 42. Electrical contact end 120 has three discreet conductive contacts 122, 123 and 124.

Figure 2:
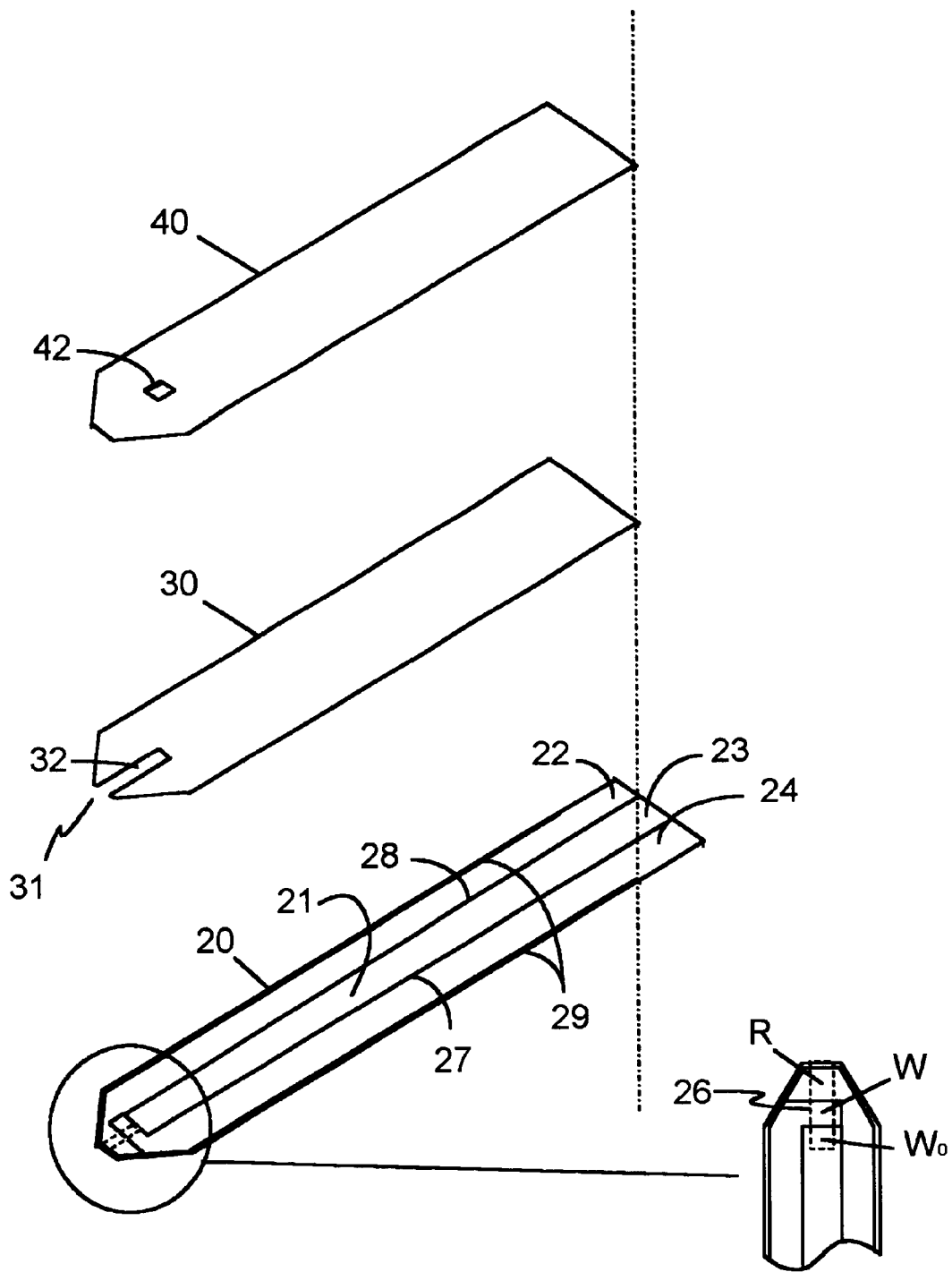
FIG. 2 is an exploded, perspective view of the present invention showing the various layers of the laminated body.

Referring now to FIG. 2, laminated body 100 is composed of a base insulating layer 20, a middle layer 30, and a top layer 40. All layers are made of a dielectric material, preferably plastic. Examples of a preferred dielectric material are polyvinyl chloride, polycarbonate, polysulfone, nylon, polyurethane, cellulose nitrate, cellulose propionate, cellulose acetate, cellulose acetate butyrate, polyester, acrylic and polystyrene. Base insulating layer 20 has a conductive layer 21 on which is delineated a first conductive conduit 22, a second conductive conduit 23 and a third conductive conduit 24. Conductive conduits 22, 23 and 24 may be formed by scribing or scoring the conductive layer 21 as illustrated in FIG. 2 and shown as scribe line 27 and 28 or by silk-screening the conductive conduits 22, 23 and 24 onto base layer 20. Scribing or scoring of conductive layer 21 may be done by mechanically scribing the conductive layer 21 sufficiently to create the three independent conductive conduits 22, 23 and 24. The preferred scribing or scoring method of the present invention is done by using a carbon dioxide ($CO_2$) laser, a YAG laser or an eximer laser.

An additional scoring line 29 (enlarged and not to scale; for illustrative purposes only) may be made, but is not necessary to the functionality of sensor 10, along the outer edge of base layer 20 in order to avoid potential static problems which could give rise to a noisy signal. Conductive layer 21 may be made of any electrically conductive material, preferably gold or tin oxide/gold. A useable material for base layer 20 is a tin oxide/gold polyester film (Cat. No. FM-1) or a gold polyester film (Cat. No. FM-2) sold by Courtaulds Performance Films, Canoga Park, Calif.

Middle layer 30 has a U-shaped channel cutout 32 located at middle layer sensor end 31. The length of channel cutout 32 is such that when middle layer 30 is layered on top of base layer 20, electrode areas W, R and $W_0$ are within the space defined by channel cutout 32. The thickness of middle layer 30 was found to be critical for the speed of the sample fluid flow into sample fluid channel 112, which is filled by capillary action of the sample fluid. Channel cutout 32 holds the reagent matrix 50, more clearly shown in FIG. 3, forming the working electrode, the reference electrode and the pseudo-working electrode. Typically, the reagent matrix 50 must be loaded with a redox mediator to make the reference electrode function. If R is not loaded with a redox reagent or mediator, working electrode W and $W_0$ will not work. Electrode areas W, $W_0$ and R are loaded preferably with the same chemical reagent. The reagents preferably contain an oxidized form of a redox mediator, a stabilizer, a binder, a surfactant, a buffer, and an enzyme. Typically, the redox mediator may be at least one of ferrocene, potassium ferricyanide, other ferrocene derivatives, or other organic and inorganic redox mediators. The preferred stabilizer is polyethylene glycol, the preferred binder is methyl cellulose, the preferred surfactant is t-octylphenoxypolyethoxyethanol, and the preferred buffer is a citrate buffer. The enzyme is capable of catalyzing a reaction involving a substrate for the enzyme or a substrate catalytically reactive with an enzyme and a mediator capable of transferring electrons transferred between the enzyme-catalyzed reaction and the working electrode to create a current representative of the activity of the enzyme or substrate and representative of the compound. An example of such an enzyme is glucose oxidase.

Figure 3:
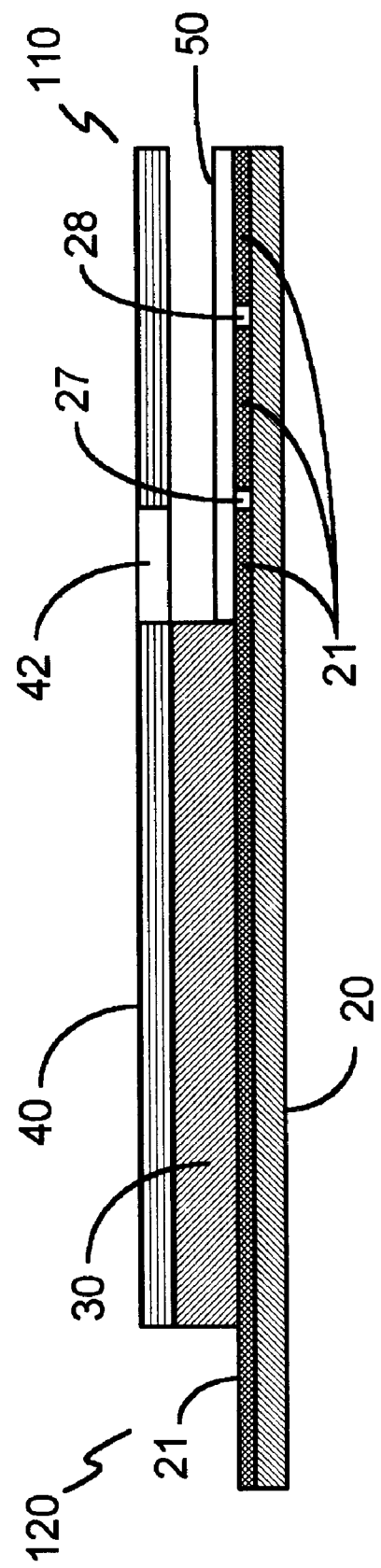
FIGS. 3 is a cross-sectional view of the present invention of FIG. 1
Figure 4:
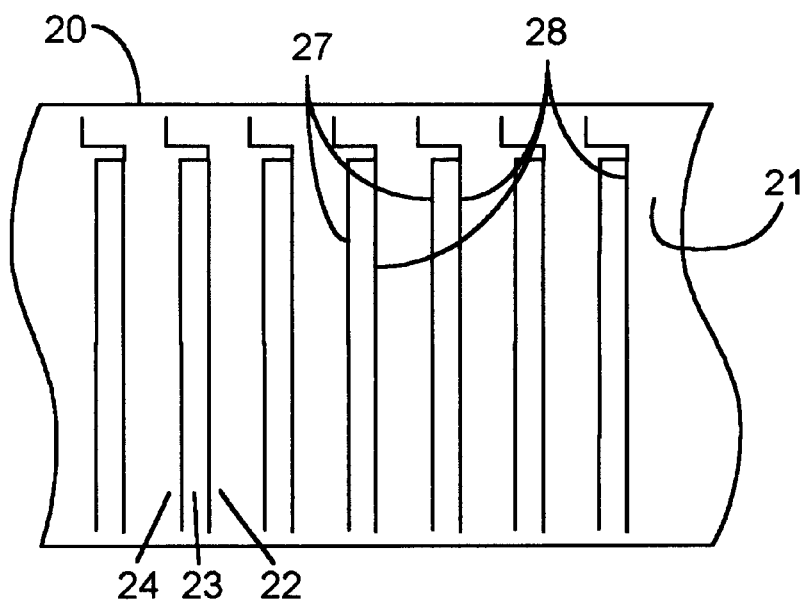
FIGS. 4A, 4B and 4C are top views of a segment of a strip of each layer of the present invention showing the patterns for making multiple sensors of the present invention.
FIG. 4D is a top view of a segment of the laminated strip of the present invention showing the patterns for making multiple sensors of the present invention.
Figure 4:
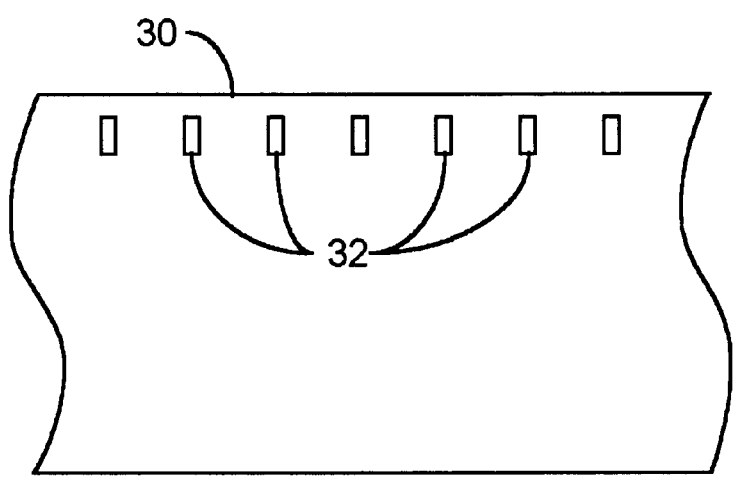
Figure 4:
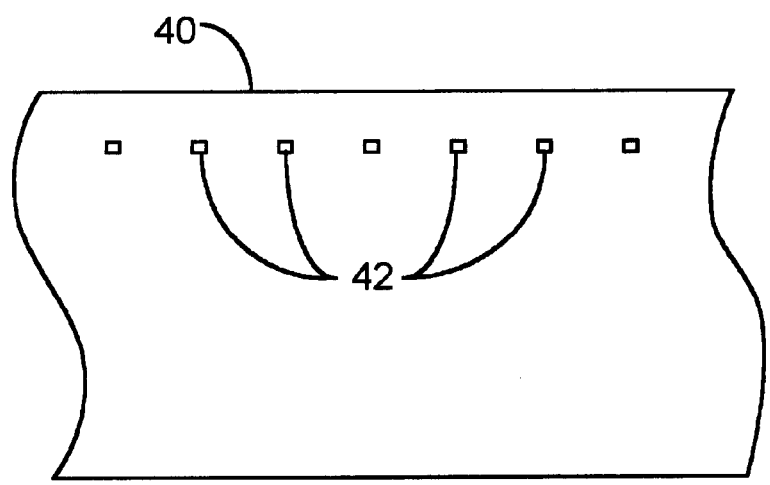
Figure 4:
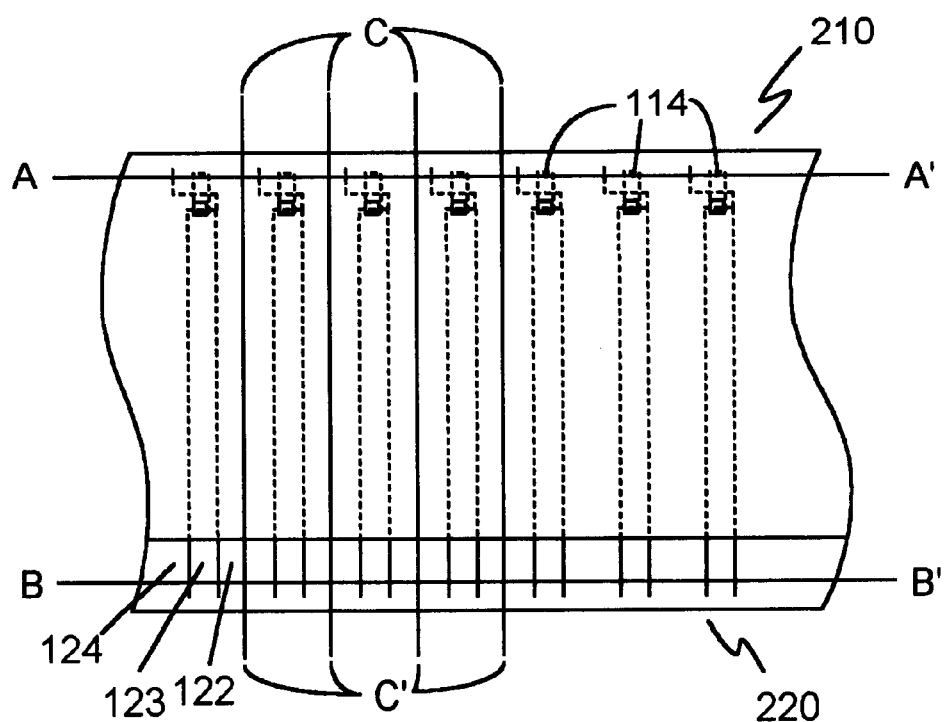

Top layer 40, which is placed over and coextensive with middle layer 30, has a vent opening 42 spaced from fluid sample end 110 of sensor 10 to insure that sample fluid in fluid channel 112 will completely cover electrode areas W, R and $W_0$. Vent opening 42 is placed in top layer 40 so that it will align somewhat with the bottom of channel cutout 32 of middle layer 30, the bottom meaning the channel cutout 32 located furthest from sensor end 31. Preferably, vent opening 42 will expose a portion of and partially overlay the bottom of the U-shaped cutout 32 of middle layer 30. FIG. 3 shows an enlarged cross-sectional view of the various layers of the present invention. The layers are not to scale in order that the relationship of each component of the present invention may be better understood by those skilled in the art, especially scribe lines 27 and 28.

Preparation of Electrode Reagent Matrix

The electrode reagent matrix comprises the oxidized form of a redox mediator, a stabilizer, a binder, a surfactant, a buffer, and an enzyme. The oxidized form of the redox mediator, potassium ferricyanide, was found to be stable in the matrix. Suitable potassium ferricyanide is available from Sigma Chemical, St. Louis, Mo. (Cat. No P3667). The quantity used in the formulation must be sufficient to attain a workable linear range. The enzyme must also have sufficient activity, purity and stability. A commercially available glucose oxidase may be obtained from Biozyme, San Diego, Calif. as Cat. No. G03A, about 270 U/mg. The stabilizer must be sufficiently water-soluble and be capable of stabilizing both the mediator and the enzyme. The preferred stabilizer is polyethylene glycol (Cat. No. P4338, Sigma Chemicals, St. Louis, Mo.). The binder should be capable of binding all other chemicals in the reagent matrix in electrode areas W, R and $W_0$ to the conductive surface/layer 21 of base layer 20. The preferred binder is Methocel 60 HG (Cat. No. 64655, Fluka Chemical, Milwaukee, Wis.). The buffer solution must have sufficient buffer capacity and pH value to optimize the enzyme reaction. A 0.05 M citrate buffer is preferred. Citric acid and sodium citrate used in making the citrate buffer may be obtained from Sigma Chemical. The surfactant is necessary to facilitate dispensing of the electrode reaction matrix into channel cutout 32 as well as for quickly dissolving the dry chemical reagents involved in forming the reagent matrix. The amount and type of surfactant is selected to assure the previously mentioned functions and to avoid a denaturing effect on the enzyme. The preferred surfactant is Triton X-100 available from Fluka Chemical, Milwaukee, Wis. (Cat. No. 94443). The reagent matrix is obtained by preparing a reagent mix as follows:

Step 1: Prepare 50 mM citrate buffer (pH 5.7) by dissolving 0.1512 grams citric acid and 1.2580 grams sodium citrate in 100 ml of deionized water.

Step 2: Prepare a 1% methocel 60 HG solution by stirring 1 gram of methocel in 100 ml of citrate buffer from Step 1 for 12 hours.

Step 3: Add 0.3 ml of 10% Triton X-100 into the methocel solution.

Step 4: Add 2.5 grams of polyethylene glycol into the solution from Step 3.

Step 5: While stirring, add 6.5 grams potassium ferricyanide to the solution of Step 4.

Step 6: Add 1.0 gram of glucose oxidase to the solution of Step 5 and stir for 10 minutes or until all solid materials are completely dissolved.

Electrode Construction

A piece of a gold or tin oxide/gold polyester film available from Courtaulds Performance Films is cut to shape, as illustrated in FIG. 2, forming base layer 20 of sensor 10. A $CO_2$ laser is used to score the gold or tin oxide/gold polyester film (25 W laser available from Synrad, Inc., San Diego, Calif.). As illustrated in FIG. 2, the film is scored by the laser creating scoring line 27 and 28 such that two electrodes at sample fluid end 110 and three contact points 122, 123 and 124 were formed at electrical contact end 120. The scoring line is very thin but sufficient to create two separate electrical conductors. An additional scoring line 29 made be made, but is not necessary, along the outer edge of base layer 20 to avoid potential static problems which could cause a noisy signal from the finished sensor 10.

A piece of double-sided tape (Arcare® 7840) available from Adhesive Research, Glen Rock, Pa., is cut to size and shape forming middle layer 30 with U-shaped channel 32 so that it will cover a majority of the conductive layer 21 of base layer 20 except for exposing a small electrical contact area at electrical contact end 120 illustrated in FIG. 1. The U-shaped channel 32 is cut by using the $CO_2$ laser. Middle layer 30 is then layered onto base layer 20. As mentioned earlier, this middle layer 30 serves as a spacer and defines the size of the fluid sample channel 112. It also defines the electrode area 26 which holds the electrode reagent matrix 50. Its width and length is optimized to provide for a relatively quick moving fluid sample. The preferred size of U-shaped channel 32 is about 0.039 in. (1.0 mm) wide by about 0.134 in. (3.4 mm) long.

1.0 microliters of reagent mix is dispensed into channel 32 to form electrodes W, R and $W_0$. The reagent mix is a mixture of a redox mediator, a stabilizer, a binder, a surfactant, a buffer, and an enzyme. The preferred composition for the reagent mix is made by mixing the following percentages (W/W%) of the following ingredients: about 6.5% potassium ferricyanide, about 2.5% polyethylene glycol, about 1% methocel 60 HG, about 0.03% Triton X-100, about 0.05 M citrate buffer (pH 5.7), and about 1% glucose oxidase. After the addition of the reagent mix, the device was dried in an oven at 55° C. for about 2 minutes.

After drying, a piece of a transparency film (Cat. No. PP2200 or PP2500 available from 3 M) is fashioned into top layer 40. A rectangular vent hole 42 is made using the $CO_2$ laser previously mentioned. The preferred size of vent hole 42 is about 0.039 in. (1.0 mm) by about 0.051 in. (1.30 mm). Vent hole 42 is located approximately 0.087 in. (2.2 mm) from fluid end 110 of sensor 10. Top layer 40 is aligned and layered onto middle layer 30 to complete the assembly, as illustrated in FIG. 1, of sensor 10.

Although the description of electrode construction above describes construction for a single sensor, the design and materials used are ideal for making multiple sensors from one piece of each layer material as shown in FIGS. 4A–4C. This is accomplished by starting with a relative large piece of base layer 20 having conducting layer 21 thereon. A plurality of scored lines 27 and 28 are made into conductive layer 21 such that a repetitive pattern, as illustrated in FIG. 4A, is created using the preferred scribing method described previously whereby each pattern will eventually define the three conductive paths 22, 23 and 24 for each sensor. Similarly, a large piece of middle layer 30 having a plurality of elongated cutouts 32 in a repetitive pattern and illustrated in FIG. 4B is layered onto base layer 20. The large piece of middle layer 30 is sized to fit over base layer 20 in such that the plurality of elongated cutouts 32 are aligned over the areas where the scribe lines 27 and 28 intersect exposing three distinct electrode areas W, R and $W_0$, and exposing the plurality of conductive contacts 122, 123 and 124 located at the opposite edge of the strip. The size of each cutout and the amount of reagent mix disposed in each channel 32 are similar to that disclosed above. After dispensing the reagent mix into the respective cutouts, the reagent mix is dried such that each elongated cutout 32 of middle layer 30 contains a thin layer of the reagent matrix. A top layer 40 comparably-sized to and coextensive with middle layer 30 having a plurality of vent openings 42 in a repetitive pattern, as shown in FIG. 4C, is layered onto middle layer 30. FIG. 4D is a top view of the combined layers. The laminated strip created by the three layers 20, 30 and 40 has a plurality of sensors 10 that can be cut from the laminated strip. The laminated strip is cut longitudinally along line A–A' at fluid sampling end 210 to form a plurality of sampling apertures 114 and longitudinally along line B–B' at electrical contact end 220 to form a plurality of conductive contacts 122, 123 and 124. The laminated strip is cut at predetermined intervals along lines C–C' forming a plurality of individual sensors 10. Shaping of the fluid sampling end 120 of each sensor 10, as illustrated in FIG. 1, may be performed if desired. It should be understood by those skilled in the art that the order in which the laminated strip can be cut is not important. For instance, the laminated strip may be cut at the predetermined intervals (C–C') and then the cuts along A–A' and B–B' can be made to complete the process.

The following examples illustrate the unique features of the present invention. All sensors of the present invention were tested on a breadboard glucose meter manufactured by Nova Biomedical Corporation of Waltham, Mass. A potential of 0.35 Volts was applied across the working electrode and the reference electrode and the resultant current signals were converted to glucose concentrations. The readings were compared to readings (control readings) obtained on the same samples using a YSI Glucose Analyzer (Model 2300) available from Yellow Springs Instruments, Inc., Yellow Springs, Ohio.

EXAMPLE 1

Demonstration of Minimum Sample Volumes Feature

Figure 5:
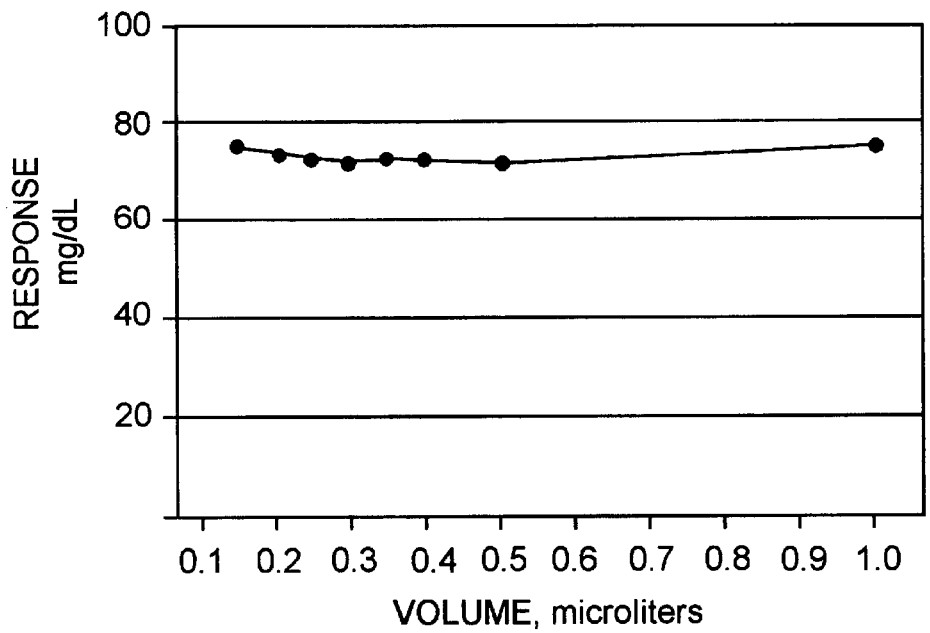
FIG. 5 is a correlation of sample volume on the concentration response of the present invention.

The unique design of the present invention enables the measurement of sample sizes smaller than which have heretofore been possible. Blood samples are applied to the sensors and the samples travel along the fluid sample channel to the venting hole. The blood volume required for measurement of blood glucose is determined by the channel volume. The calculated volume for the present invention is 0.22 microliters. In order to test the volume effect on sensor response, different blood sample volumes were applied to the sensors and the resulting concentration readings were plotted against volume. The test data is shown in FIG. 5.

Sensors of the present invention show no dependence of the response on the sample volume down to a volume of less than 0.22 microliters. It was found that sensors of the present invention still gave reasonable readings on sample sizes as low as 0.15 microliters. This is possible because the hydrophilic character of the Reagent Matrix applied to W, R and $W_0$ permitted the sample to cover the electrode areas even though the blood volume did not fill the entire sample channel.

EXAMPLE 2

Demonstration of Wide Linear Range and Precision Feature

Figure 6:
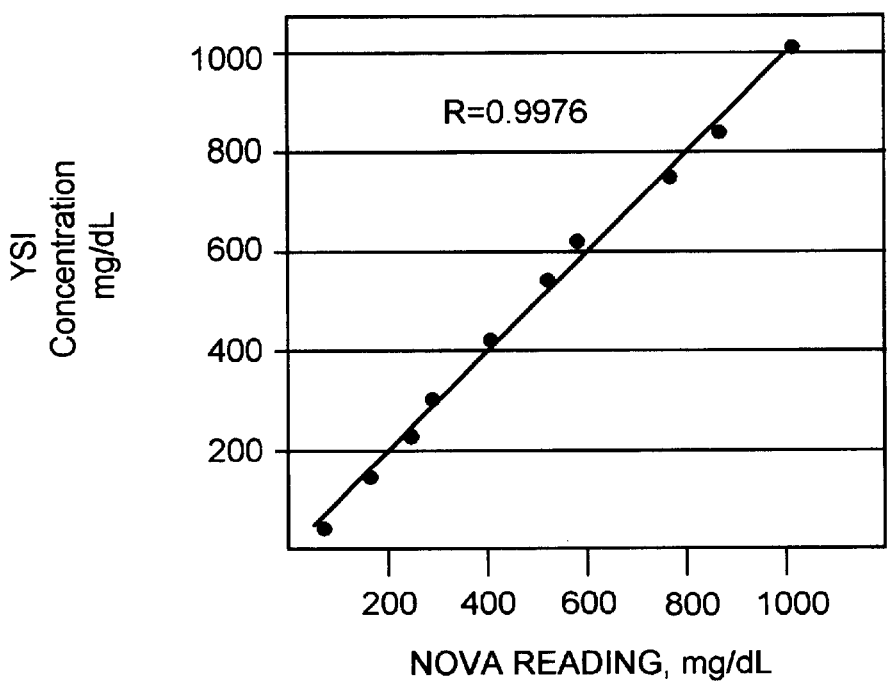
FIG. 6 is a correlation curve of the concentration readings using sensors of the present invention versus the concentration readings of obtained on the same samples using a YSI glucose analyzer.

A sample of venous blood was collected and separated into several aliquots. Each aliquot was spiked with different glucose concentrations ranging from 35 to 1000 mg/dL. The aliquots were each measured with a YSI glucose analyzer and then with sensors of the present invention using the Nova glucose meter. Sensors of the present invention show a linear relationship of current response vs. glucose concentration from 35 to 1000 mg/dL. The concentration readings were plotted against the concentration values obtained using the YSI meter (the control) and are illustrated in FIG. 6.

A regression coefficient of 0.9976 indicated a near perfect match with the readings obtained with the YSI blood glucose analyzer. The same aliquots were tested using four different commercially-available sensors with their accompanying meters. The commercially-available sensors showed a linear response only up to about 600 mg/dL. Above the 500–600 mg/dL range, all commercially available sensors displayed "Hi" as the test result.

The precision of the sensors of the present invention was investigated at the same glucose level range from about 35 to 1000 mg/dL. Four different batches of sensors of the present invention were used in the precision tests. Typically, the relative standard deviation was about 5.0% and 3.6% for samples containing 100 and 300 mg/dL levels of glucose, respectively.

What is claimed is:

1. A disposable electrode strip for testing a fluid sample comprising:
   a laminated strip having a first strip end, a second strip end and a vent opening spaced from said first strip end, said laminated strip comprising a base layer having a conductive layer disposed thereon, said conductive layer having a scribe line delineated thereon and forming three electrode paths, a channel forming layer carried on said base layer, and a cover;
   an enclosed channel between said first strip end and said vent opening, said enclosed channel sized to hold a volume of said fluid sample less than one microliter;
   a reagent matrix containing at least an enzyme; a stabilizer, wherein said stabilizer is a polyalkylene glycol; and a redox mediator disposed on said base layer in said enclosed channel;
   conductive contacts at said second strip end and insulated from said enclosed channel.

2. The electrode strip of claim 1 wherein said enzyme is glucose oxidase.

3. The electrode strip of claim 1 wherein said redox mediator is at least one metal complex.

4. The electrode strip of claim 3 wherein said redox mediator is at least one of potassium ferricyanide or other inorganic or organic redox mediators.

5. The electrode strip of claim 1 wherein said conductive coating is gold.

6. The electrode strip of claim 1 wherein said conductive coating comprising gold and tin oxide.

7. The electrode strip of claim 1 wherein said base layer, said channel forming layer and said cover are made of a plastic dielectric material.

8. The electrode strip of claim 1 wherein said enclosed channel is hydrophilic.

9. The electrode strip of claim 1 wherein said enclosed channel has a volume of about 0.22 microliters.

10. The electrode strip of claim 1 wherein said cover has a hydrophilic coating on at least one side.

11. The electrode strip of claim 1 wherein said reagent matrix further contains at least one of, a binder, a surfactant, and a buffer.

12. The electrode strip of claim 11 wherein, said binder is a cellulose material, and said surfactant is a polyoxyethylene ether.

13. The electrode strip of claim 12 wherein said stabilizer is polyethylene glycol, said binder is methyl cellulose, said surfactant is t-octylphenoxypolyethoxyethanol, and said buffer is a citrate buffer.

14. The electrode strip of claim 13 wherein said reagent matrix is made from a mixture having starting components comprising about 1 wt % to about 6.5 wt % of said redox mediator, about 2.5 wt % of said stabilizer, about 1 wt % of said binder, about 0.03 wt % of said surfactant, and about 1 wt % of said enzyme in said citrate buffer.

15. The electrode strip of claim 14 wherein said citrate buffer is about 0.05 M.

16. The electrode strip of claim 14 wherein said potassium ferricyanide is 6.5 wt %.

17. The electrode strip of claim 14 wherein said enzyme is glucose oxidase.

18. The electrode strip of claim 1 wherein said channel forming layer thickness sufficient to optimize the flow of said fluid sample along said open path.

19. The electrode strip of claim 18 wherein said thickness is about 0.0035 inches (0.089 mm).

20. The electrode strip of claim 1 wherein said enclosed channel contains a working electrode, a pseudo-working electrode and a reference electrode.

21. The electrode strip of claim 20 wherein said pseudo-working electrode is a counter electrode.

22. The electrode strip of claim 20 wherein said pseudo-working electrode is a triggering electrode.

23. The electrode strip of claim 20 wherein said pseudo-working electrode and said reference electrode pair are a resistance-measuring electrode pair.

24. The electrode strip of claim 1 wherein said stabilizer is polyethylene glycol.

25. A disposable electrode strip for detecting or measuring the concentration of an analyte in a fluid sample, said electrode strip comprising:
   an insulating base strip having a first base end and a second base end;
   a conductive layer disposed on one side of said base strip, said conductive layer having a pattern scribed into said conductive layer, said pattern delineating three electrically-distinct conductive paths insulated from each other;
   a middle insulator sized smaller than said insulating base strip and overlaying a substantial portion of said conductive layer, said middle insulator having a cutout portion spaced from said first base end, said cutout portion exposing a limited area of said three conductive paths;
   an electrode material comprising an enzyme, a redox mediator; a stabilizer, wherein said stabilizer is a polyalkylene glycol, a binder, a surfactant, and a buffer, said electrode material being disposed in said cutout portion; and
   a covering insulator sized to fit over and be coextensive with said middle insulator creating a sample fluid channel, said covering insulator having a covering insulator aperture spaced from said first base end and configured to expose at least a small portion of said cutout portion of said middle insulator.

26. The strip of claim 25 wherein said sample fluid channel has a volume of about 0.22 microliters.

27. The strip of claim 25 wherein said sample fluid channel is hydrophilic.

28. The strip of claim 25 wherein said redox mediator is at least one metal complex selected from the group consisting of ferrocene, ferrocene derivatives and potassium ferricyanide, said stabilizer is a polyalkylene glycol, said binder is a cellulose material, said surfactant is a polyoxyethylene ether, and said buffer has a pH of about 5 to about 6.

29. The strip of claim 28 wherein said mediator is potassium ferricyanide, said stabilizer is polyethylene glycol, said binder is methyl cellulose, said surfactant is t-octylphenoxypolyethoxyethanol, and said buffer is a citrate buffer.

30. The strip of claim 29 wherein said electrode material is made of a mixture having starting components comprising about 6.5 wt % of said potassium ferricyanide, about 2.5 wt % of said polyethylene glycol, about 1 wt % of said methyl cellulose, and about 0.03 wt % of said t-octylphenoxypolyethoxyethanol, and about 1 wt % of said enzyme in said citrate buffer.

31. The strip of claim 30 wherein said enzyme is glucose oxidase.

32. The electrode strip of claim 25 wherein said sample fluid channel contains a working electrode, a pseudo-working electrode and a reference electrode.

33. The electrode strip of claim 32 wherein said pseudo-working electrode is a counter electrode.

34. The electrode strip of claim 32 wherein said pseudo-working electrode is a triggering electrode.

35. The electrode strip of claim 32 wherein said pseudo-working electrode and said reference electrode pair are a resistance-measuring electrode pair.

36. A method of making multiple, disposable sensors wherein each sensor has at least a working electrode, a reference electrode, a pseudo-working electrode, and a reagent matrix, wherein said reagent matrix contains an enzyme capable of catalyzing a reaction involving a substrate for the enzyme, said working electrode and said reference electrode being disposed in a fluid sample channel for measuring a fluid sample, said method comprising:

obtaining a base strip of an insulating material having a layer of conductive material disposed thereon, said base strip having a first edge and a second edge;

scribing in said conductive material a plurality of lines in a repetitive pattern wherein said plurality of lines contain a repetitive pattern capable of forming three conductive paths in each of said repetitive pattern;

disposing a middle layer of insulating material over said base strip, said middle layer having a repetitive pattern of an elongated cutout wherein each cutout of each of said repetitive pattern exposes an electrode portion of each of said three conductive paths of each repetitive pattern wherein said repetitive pattern of said elongated cutout are spaced from said first edge of said base strip, and wherein said middle layer is sized to expose a contact portion of each of said two conductive paths of each repetitive pattern for a distance from said second edge of said base strip;

disposing an reagent material, wherein said reagent material contains a polyalkylene glycol stabilizer, into each elongated cutout of said repetitive pattern;

drying said reagent material at a temperature and for a length of time sufficient to solidify said reagent material in each of said elongated cutout;

disposing a top layer of insulating material over and coextensive with said middle layer, said top layer having a plurality of vent openings in a repetitive pattern wherein each of said vent openings exposes a portion of a corresponding repetitive pattern of said elongated cutout of said middle layer furthest from said first edge of said base strip, said base strip, said middle layer and said top layer forming a laminated strip;

cutting along and parallel to said first edge of said laminated strip a predetermined distance creating a sample inlet port in each of said elongated cutout for each of said repetitive pattern;

cutting along and parallel to said second edge of said laminated strip a predetermined distance creating two separate contacts for each of said repetitive pattern; and separating each of said repetitive pattern at predetermined intervals along said laminated strip.

37. The method of claim 36 wherein said drying step further includes heating said reagent material at a temperature of about 55° C.

38. The method of claim 37 wherein said drying step further includes heating said reagent material for about two minutes.

* * * * *